United States Patent
Cabrera

(10) Patent No.: US 7,112,336 B2
(45) Date of Patent: Sep. 26, 2006

(54) SOLID PHASE DISPERSION OF QUINOLONE OR NAPHTHYRIDONECARBOXYLIC ACIDS

(75) Inventor: Francisco Cabrera, Overland Park, KS (US)

(73) Assignee: Bayer HealthCare LLC, Tarrytown, NY (US)

( * ) Notice: Subject to any disclaimer, the term of this patent is extended or adjusted under 35 U.S.C. 154(b) by 5 days.

(21) Appl. No.: 10/835,804

(22) Filed: Apr. 30, 2004

(65) Prior Publication Data

US 2004/0204442 A1    Oct. 14, 2004

Related U.S. Application Data

(63) Continuation of application No. 09/768,657, filed on Jan. 24, 2001, now abandoned.

(51) Int. Cl.
*A61K 47/00* (2006.01)
*A61K 9/14* (2006.01)
*A23K 1/165* (2006.01)

(52) U.S. Cl. ............... 424/439; 424/442; 424/484; 424/485; 424/489

(58) Field of Classification Search ............... 424/439, 424/442, 485, 489, 484
See application file for complete search history.

(56) References Cited

U.S. PATENT DOCUMENTS

| | | |
|---|---|---|
| 5,152,986 A | 10/1992 | Lange et al. |
| 5,281,596 A | 1/1994 | Kitao et al. |
| 5,695,784 A * | 12/1997 | Pollinger et al. |
| 5,808,076 A | 9/1998 | Vetter et al. |

* cited by examiner

*Primary Examiner*—Humera N. Sheikh
(74) *Attorney, Agent, or Firm*—Susan M. Pellegrino

(57) ABSTRACT

The present invention relates to a solid dispersion of quinolone- or naphthyridonecarboxylic acids in an insoluble matrix representative of a shellac, and methods preparing and using the same in masking the taste and improving the uptake by animals.

6 Claims, No Drawings

SOLID PHASE DISPERSION OF QUINOLONE OR NAPHTHYRIDONECARBOXYLIC ACIDS

This application is a Continuation application of Ser. No. 09/768,657 filed Jan. 24, 2001, now abandoned.

FIELD OF THE INVENTION

The present invention relates to the preparation of orally administrable formulations of quinolone- or naphthyridonecarboxylic acids and methods of making and using the same. More specifically, the invention relates to quinolone- or naphthyridonecarboxylic acids in a solid phase dispersion, which masks their bitter taste.

BRIEF DESCRIPTION OF THE PRIOR ART

Quinolonecarboxylic acids and their formulations are already known. See, for example, EP-A (European Published Specification) 238 814. Of particular interest here are formulations that are intended to mask the bitter taste of the active quinolone compounds. U.S. Pat. No. 5,808,076 discloses a method of preparing an improved oral formulation of quinolone compounds by mixing the quinolones in the form of their aqueous solution salts or derivatives with embonic acid. U.S. Pat. No. 5,152,986 discloses a method of preparing and using ion exchange resins loaded with quinolonecarboxylic acid derivatives.

It has now been found that orally administrable formulations of quinolone- or naphthyridonecarboxylic acids can be obtained with solid phase dispersions of quinolone- or naphthyridonecarboxylic acids in an insoluble matrix.

DESCRIPTION OF THE INVENTION

In accordance with the foregoing, the present invention encompasses solid phase dispersion of an active ingredient of quinolone- or naphthyridonecarboxylic acid in an insoluble matrix in an effective amount to mask the taste of the active ingredient. Also encompassed by the invention is a process for preparing the solid phase dispersion by admixing quinolone- or naphthyridonecarboxylic acids with an insoluble matrix to produce a solid dispersion. Preferably, the quinolone- or naphthyridonecarboxylic acid is employed in a micronized form and more preferably in the form of fine powder, and the insoluble matrix is employed in the form of flakes or powder. In a presently preferred embodiment of the invention, these two components are first admixed by comminuting them by say pulverizing micronized quinolone- or naphthyridonecarboxylic acid with flakes of shellac. This is followed by further mixing and addition of water to form a hydrate, and by, say, melt mixing, and further comminuting to reduce particle size to provide the desired solid phase dispersion. By the term solid dispersion is meant quinolone- or naphthyridonecarboxylic acid finely divided particles are distributed throughout the insoluble matrix.

It has surprisingly been found that the solid phase dispersion in accordance with this invention provides greatly reduced quinolone- or naphthyridonecarboxylic acid particle size. It has also been found that the dispersion provides acceptable solubility of the quinolone- or naphthyridonecarboxylic acid. It has also been found that the dispersion provides controlled release of the quinolone- or naphthyridonecarboxylic acid, which can be administered orally without any problems even to animals which will normally refuse formulations containing quinolone- or naphthyridone-carboxylic acid owing to their bitter taste. Unexpectedly, the solid phase dispersion has an outstanding acceptance when administered.

Quinolone- or naphthyridonecarboxylic acids and derivatives are known. See, for example, EP-A (European Published Specification) 350 950, 302 372, 49 355, 47 005, 242 789, 259 804, 215 650, 131 839, 109 284; DE-A (German Published Specification) 2 804 097; FR-P (French Patent Specification) 2 463 771; PCT WO 92/9596. (The formulae and the specific compounds mentioned in these publications are incorporated herein by reference.)

Preferred compounds are temafloxacin, tosufloxacin, enrofloxacin, ciprofoxacin, ofloxacin, orbifloxacin, marbofloxacin, norfloxacin, benofloxacin, binfloxacin, danofloxacin, difloxacin, sarafloxacin, premafloxacin and ibafloxacin. Particularly preferred compounds are: enrofloxacin, danofloxacin and sarafloxacin. Derivatives of these active compounds include their esters such as the $C_1$-$C_4$-alkyl esters. Salts of these active compounds include all salts with acids forming physiologically acceptable salts. These include hydrohalic acids, sulfonic acids, carboxylic acids, amino acids, (poly)-hydroxycarboxylic acids, phosphonic acid, nitric acid and sulfuric acid. Specifically, these are methanesulfonic acid, ethanesulfonic acid, hydroxyethanesulfonic acid, benzenesulfonic acid, p-toluenesulfonic acid, formic acid, acetic acid, propionic acid, dimethylolpropionic acid, hydroxyacetic acid, lactic acid, hydroxymaleic acid, oxalic acid, succinic acid, fumaric acid, maleic acid, glutaric acid, malonic acid, adipic acid, ascorbic acid, malic acid, citric acid, tartaric acid, aminosalicyclic acid, anthranilic acid, benzoic acid, hydroxybenzoic acid, phenylacetic acid, salicylic acid, phthalic acid, nicotinic acid, mandelic acid, aspartic acid, glutamic acid, gluconic acid, glucuronic acid, latobionic acid, galaturonic acid, mucic acid, phosphoric acid, nitric acid, hydrochloric acid, sulfuric acid, 5-oxotetrahydrofuran-2-carboxylic acid and 2-hydroxyglutaric acid. Particular preference is given to hydrochloric acid or gluconic acid.

Suitable bases for forming salts with quinolones or naphthyridonecarboxylic acid are, for example, the following: alkali metal and alkaline earth metal hydroxides, such as KOH, NaOH, $Ca(OH)_2$, ammonia, basic amino acids such as arginine, lysine, choline, N-methylglucamine, ethylenediamine, mono-, di-trialkylamines, substituted amines such as, for example, diethanolamine and cyclic amines such as, for example, morpholine, piperazine, tromethamol (=tris (hydroxymethyl)-aminomethane). Particularly suitable are KOH, arginine, lysine and N-methyl-glucamine.

The insoluble matrix can be characterized as a material in which the quinolone- or naphthyridonecarboxylic acid is so embedded that it masks the taste of the quinolone- or naphthyridonecarboxylic acid and yet allows the same to be leached out and made pharmaceutically available to animals consuming the solid disperson. The quionolone- or naphthyridonecarboxylic acid can be made available to the target species as it dissolves in say the intestinal fluid, and is absorbed into the blood stream. Illustrative but non-limiting examples of the insoluble matrix can be selected from the group consisting of shellac, polyvinyl alcohol, poly (D,L-lactic-co glycolic) acid, sugars, and polyethylene glycol, which is preferably of high molecular weight. Preferred herein is shellac, especially in form of flakes.

Suitable excipients, carriers and/or auxiliaries, which are preferably organic or inorganic inert solid substances can be formulated with the solid phase dispersion. Inorganic and organic substances may be used in this capacity. Examples of inorganic substances are: common salt, carbonates (for example, calcium carbonic), hydrogencarbonates, aluminum oxides, silicas, clays, precipitated or colloidal silicon dioxide and phosphates. Examples of organic substances are sugar and optionally their derivatives, polyethylene glycols, paraffins, and fatty acids.

As a carrier, one can use a mixture of the substances mentioned in addition to cellulose and its derivatives, starches (for examples corn, rice, potato, tapioca, or wheat starch), foodstuffs and feeds such as, for example milk powder, animal meal, ground and bruised grain. Other carriers, which in addition have the property of binding water can be employed. Example thereof are carboxymethyl cellulose, methyl cellulose and other cellulose and starch derivatives, polyacrylates, alginates, gelatin, chitin, gum arabic, polyvinylpyrrolidone, polyvinyl alcohols, copolymers of vinyl ether and acid anhydrides, polyethylene glycols, waxes, colloidal silicas or mixtures of the substances and classes of substances mentioned.

Auxiliaries such as preservatives, antioxidants, photostabilizers, colorants, absorption-promoting substances, disintegration-promoting substances, binders or lubricants and stabilizers may be used.

The method according to the invention comprises mixing the individual components. Any convenient mixer, including high intensity mixers having chopping devices can be employed. The following is a non-limiting description of a method of preparation. The components can be mixed together and passed through a cone-mill with a sieve size of 1.0–8.0 mm at 500 to 800 rpm, to give a fine homogeneous powder. Illustratively, micronized quinolone- or naphthyridonecarboxylic acid and shellac flakes are mixed. The resulting mixture is heated until it melts and flows, typically at about 125 to 135° C. The mixture is then extruded or poured as a sheet and cooled rapidly to give a solid wherein the quinolone- or naphthyridonecarboxylic acid is dispersed or dissolved in the solid matrix of the shellac. The solid is then reduced in size by means of a mill to give particles between 20 to 100 mesh sizes depending on the intended use.

Where excipients, carriers or auxiliaries are required, the particles can be mixed with a suitable excipient to give an end product. Alternately, the excipients, carriers or auxiliaries can be charged initially in a conventional mixer and mixed. To this mixture, the quinolone- or naphthyridonecarboxylic acid embedded in the insoluble matrix is added. The thus-obtained mixture is then admixed using mixers including high intensity mixers having chopping devices. The ratio of quinolone- or naphthyridonecarboxylic acid to the insoluble matrix in the solid dispersion prepared according to this invention is about 1:0.5 to 10, preferably 1:2 to 8, more preferably 1:5.

As set forth above, solid dispersion can be extruded or pelletized or in powdered form. The formulations according to the invention can be applied dry on food pellets. One can employ therewith suitable binders, for example, vegetable, animal or synthetic oils, fats, fatty acids, fatty alcohols, waxes and gelatine. The formulations prepared according to the invention can, inter alia, also be filled into capsules, the capsule wall being made of hard or soft gelatin. The capsule can, if appropriate, be enteric-coated.

The formulations prepared by the process according to the invention can be used as such or in a formulation adapted to the prophylaxis or therapy of diseases in humans or target animals, in particular the treatment of bacterial infections. They are especially suitable for use in the fields of geriatrics and pediatrics or in veterinary practice in taste-sensitive animals, such as, for example, cats and pigs. In effect, the invention provides a process for improving animal "uptake" of the quinolone- or naphthyridonecarboxylic acid by animals, by providing it in a solid dispersion of an insoluble matrix, such as shellac.

The dispersions and formulations thereof are active against microrganisms pathogenic to humans and animals. These microorganisms include:

1. *Spirochaetaceae* (for example, *Treponema, Leptospira* and *Borrelia*)
2. *Spirillaceae*
3. *Micrococcaceae* (for example, *staphylococci* of biotype A–F and *St. hyicus*)
4. *Streptococcacease* (for example, *Streptococcus uberis. Str. Equi. Str. agalactiae, Str. dysgalactiae* and *streptococci* of the Lancefield groups A–N)
5. *Pseudomonaceae* (for example, *Pseudomonas malei, Ps. cepacia, Ps. aeruginosa, Ps. maltophilia), Brucella*, such as *Brucella abort, B. melitensis, B. suis* and *Bordetella*, such as *Bordetella bronchiseptica, Moraxella, Acinetobacter*)
6. *Enterobacteriaceae* (for example, *Salmonella* of the types B–E, *Shigella, E. coli, Klebsiella, Proteus, Citrobacter, Edwardsiella, Haemophilus, Providencia* and *Yersina*)
7. *Vibronaceae* (for example, *Bribrio* such as *Vibrio chloerae*), *Pasteurella* such as *Pasteurella multocia, Aeromonas, Actinobacillus* and *Streptobacillus*)
8. *Bacteroidaceae* (for example, *Bacteroides, Fusobacterium*)
9. *Erysiphylothix* and *Listeria* such as *Listeria monocytojenes*
10. *Bacillaceae* (for example, *Bacillus, Closteridium* types A–D, such as *Clostridium perfringens), Lactobacillaceae* and also anaerobic cocci such as, for example, *Peptostreptococci* and *Peptococci*
11. *Coryneform* bacteria (for example, *Corynebacterium pyogenes*)
12. *Mycobacteriaceae* (for example, *Mycobacterium bovis, M. avium*, and *M. tuberculosis*)
13. *Actinomyceae* (for example, *Actinomyces bovis* and *A. israelii*)
14. *Nocardiaceae* (for example, *Norcardia facinica* and *N. asteroides*)
15. *Rickettsjaceae* (for example, *Coxiella* and *Rickettsia*)
16. *Bartonellaceae* (for example, *Baronella*)
17. *Chlamydiaceae* (for example, *Chlamydia psittaci*)
18. *Mycoplasmataceae* (for example, *Mycoplasma mycoides, M. agalactiae* and *M. gallisepticum*)

Microorganisms pathogenic to humans and animals can cause disease symptoms in mono- or mixed infections of the following animal organ systems: lungs and intratracheal lumen, digestive systems such as stomach and intestine, breast and udder, genital system such as uterus, soft tissue such as skin, muscles, nails, claws, hoofs, active and passive locomotive system such as bones, muscles, sinews, joints and urogenital system such as kidney, urethra, ureter, nervous system, ears, eyes and gills.

As already mentioned, the formulations are used to fight bacterial diseases in humans and animals. The animals include: mammals, such as, for example, cattle, horses, pigs, sheep, goats, dogs, cats, camels, animals such as mink, chinchilla, zoo animals and laboratory animals such as, for example, mice and rats; birds, such as, for examples, geese, chickens, turkeys, ducks, pigeons, aviary birds, laboratory birds, such as, for example, parrots and budgerigars; reptiles, such as, for example, crocodiles, snakes, frogs; crustaceans, such as, for example, *Penaeidae*; for example P. monodon, crabs, lobsters.

The bacterial diseases of animals include: swine dysentery, *spirochactosis* in fowl, *leptospirosis* in cattle, swine, horses, dogs: Campylobacter-induced enteritis in cattle; Campylobacter-induced abortion in sheep and swine; Campylobacter-induced hepatitis in chicken, infections of the skin; pyoderma in dogs, otitis externa; mastitis in cattle, sheep and goats; *streptococcal* mastitas, *streptococcal* infections of the horse, of pigs and other kinds of animals; *pneumococcal* infections of the calf, and of other kinds of animals; glanders; conjunctivitis; enteritis; pneumonia; *brucellosis* in cattle, sheep, swine; *stropic rhinitis* of swine; *salmonellosis* in cattle, horses, sheep, chicken and other kinds of animals; *septicemia; Escherichia coli* infections in piglets; *metritis*-mastitis-agalactic-(MMA)-syndrome; *Klebsiella* infections; *pseudotuberculosis*; contagious *pleuropneumonia*; primary *pasteurelloses*; foal ataxia; *necrobacillosis* in cattle and pets; *leptospirosis; erysipelas* of swine and other kinds of animals; *listeriosis*; anthrax; *clostridioses*; tetanus infections; botulism; infections with *Corynebacterium pyogenes*; tuberculosis in cattle, swine, fowl and other kinds of animals; *paratuberculosis* of the ruminants; *nocardiosis;* Q fever; *ornithosis-psittacosis; encephalomycelitis; mycoplasmosis* of cattle and other animals and porcine enzootic pneumonia.

The invention is further described by the following illustrative but non-limiting examples.

EXAMPLES

Example 1

1. Mix 10 parts micronized enrofloxacin and 90 parts shellac (orange R49) flakes.
2. Pulverize in a cone mill, or comminuting mill to reduce particle size to 100 USP mesh.
3. Put in a steel pan heated on an oil bath, or with a heating mantle, or preferably run through an extruder.
4. Heat the mass to 125–134° C. with mixing until a homogeneous melt is obtained.
5. Cool to room temperature and pulverized to pass through a desired mesh size (20–100 USP).
6. Mix with suitable excipients to give the end product (medicated feed, oral suspension, or paste.

Example 2

1. Mix 10 parts enrofloxacin, 80 parts shellac flakes or powder, and 10 parts sorbitol.
2. Pulverize in a cone mill, or comminuting mill to reduce particle size to 100 USP mesh.
3. Put in a steel pan heated on an oil bath, or with a heating mantle, or preferably run through an extruder.
4. Heat the mass to 125–134° C. with mixing until a homogeneous melt is obtained.
5. Cool to room temperature and pulverized to pass through a desired mesh size (20–100 USP).
6. Mix with suitable excipients to give the end product (medicated feed, oral suspension, or paste.

Example 3

1. Mix 12.5 parts enrofloxacin, 36.1 parts sodium chloride, and 51.4 shellac flakes or powder.
2. Pulverize in a cone mill, or comminuting mill to reduce particle size to 100 USP mesh.
3. Put in a steel pan heated on an oil bath, or with a heating mantle, or preferably run through an extruder.
4. Heat the mass to 125–134° C. with mixing until a homogeneous melt is obtained.
5. Cool to room temperature and pulverized to pass through a desired mesh size (20–100 USP).
6. Mix with suitable excipients to give the end product (medicated feed, oral suspension, or paste.

Example 4

1. Mix 20 parts enrofloxacin, 10 parts carbowax 8000, and 70 parts shellac flakes or powder.
2. Pulverize in a cone mill, or comminuting mill to reduce particle size to 100 USP mesh.
3. Put in a steel pan heated on an oil bath or with a heating mantle, or preferably run through an extruder.
4. Start mixing and heating to 50° C., add 24 parts of water.
5. Heat the mass to 125–134° C. with mixing, until a homogeneous melt is obtained.
6. Cool to room temperature and pulverized to pass through a desired mesh size (20–100 USP).
7. Mix with suitable excipients to give the end product (medicated feed, oral suspensions, or paste).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A solid phase dispersion comprising a micronized quinolinecarboxylic acid or micronized naphthyridonecarboxylic acid in an insoluble matrix, wherein the insoluble matrix is shellac and wherein the particle size of the solid dispersion is about 20 to about 100 mesh size.

2. The dispersion of claim 1, wherein quinolinecarboxylic acid or naphthyridonecarboxylic acid and the insoluble matrix are in a ratio of 1:0.5 to 10.

3. The dispersion of claim 2, wherein quinolinecarboxylic acid or naphthyridonecarboxylic acid and the insoluble matrix are in a ratio of 1:5.

4. A method of preparing a solid dispersion of a quinolinecarboxylic acid or naphthyridonecarboxylic acid, comprising forming a hydrate of micronized quinolinecarboxylic acid or micronized naphthyridonecarboxylic acid, mixing the quinolinecarboxylic acid or naphthyridonecarboxylic acid with an insoluble matrix, wherein the soluble matrix is shellac, heating the mixture until it flows, and micronizing the mixture to reduce particle size, wherein said particle size is about 20 to about 100 mesh size.

5. A feed formulation comprising feedstuff and the solid phase dispersion of claim 1.

6. A process for improving animal uptake of quinolinecarboxylic acid or naphthyridonecarboxylic acid comprising orally administering to the animal a solid phase dispersion of claim 1 in an effective amount to mask the taste of the active agent.

\* \* \* \* \*